United States Patent
Lee et al.

(10) Patent No.: US 7,015,018 B1
(45) Date of Patent: Mar. 21, 2006

(54) AMPLIFICATION METHOD FOR DETECTION OF TARGET NUCLEIC ACIDS INVOLVING-FLUORESCENCE ENERGY TRANSFER

(75) Inventors: Martin Alan Lee, Salisbury (GB); Dario Lyall Leslie, Salisbury (GB)

(73) Assignee: The Secretary of State for Defence in Her Brittanic Majesty's Government of the United Kingdom of Great Britain and Northern Ireland., Salisbury (GB)

( * ) Notice: Subject to any disclaimer, the term of this patent is extended or adjusted under 35 U.S.C. 154(b) by 704 days.

(21) Appl. No.: 10/048,752

(22) PCT Filed: Aug. 3, 2000

(86) PCT No.: PCT/GB00/03016

§ 371 (c)(1),
(2), (4) Date: Jan. 31, 2002

(87) PCT Pub. No.: WO01/11078

PCT Pub. Date: Feb. 15, 2001

(30) Foreign Application Priority Data

Aug. 4, 1999 (GB) .................................. 9918237

(51) Int. Cl.
*C12Q 1/68* (2006.01)
*C12P 19/34* (2006.01)
*C07H 21/02* (2006.01)

(52) U.S. Cl. ...................... 435/91.2; 435/6; 435/91.1; 536/23.1; 536/24.3; 536/24.31; 536/24.33

(58) Field of Classification Search ............... 435/6, 435/91.1, 91.2; 536/23.1, 24.3, 24.31, 24.33
See application file for complete search history.

(56) References Cited

U.S. PATENT DOCUMENTS 6,117,635 A * 9/2000 Nazarenko et al. ............. 435/6
6,287,781 B1 * 9/2001 Lee et al. ....................... 435/6
6,326,145 B1 * 12/2001 Whitcombe et al. .......... 435/6
6,440,675 B1 * 8/2002 Lindblad-Toh et al. ........ 435/6

FOREIGN PATENT DOCUMENTS

| EP | 0566751 | 10/1993 |
| GB | 2333596 | 7/1999 |
| WO | WO 98/02449 | 1/1998 |
| WO | WO 99/42611 | 8/1999 |
| WO | WO 99/66071 | 12/1999 |

OTHER PUBLICATIONS

Chen et al (Proc. Natl. Acad. Sci. (1997) 94: 10756-10761).*
S. Wliton, et al., "Snapback SSCP Analysis: Engineered Conformation Changes for the Rapid Typing of Known Mutations," Human Mutation, vol. 11, pp. 252-258 (1998).
Z. Zhu, et al., "Molecular Mechanism Controlling the Incorporation of Fluorescent Nucleotides Into DNA by PCR," Cytometry, vol. 28, pp. 206-211 (1997).
Hiyoshi et al., "Assay of DNA Danaturation by Polymerase Chain Reaction-Driven Fluorescent Label incorporation and Fluorescence Resonance Energy Transfer", Analytical Biochemistry, 221 (1994) Sep., No. 2, pp. 306-311.

* cited by examiner

*Primary Examiner*—Jeffrey Fredman
(74) *Attorney, Agent, or Firm*—Kilpatrick Stockton LLP

(57) ABSTRACT

A method for detecting the presence of a target nucleic acid sequence in a sample, said method comprising subjecting said sample to an amplification reaction using a set of nucleotides, at least one of which is labelled with a first label, and a reagent comprising an amplification primer which can hybridise to said target sequence when in single stranded form and which is connected at its 5' end to a probe which carries a second label by way of a chemical linking group, said labelled probe being of a sequence which is similar to that of the said target sequence, such that it can hybridise to a complementary region in an amplification product, and wherein one of the first or the second label comprises a donor label and the other comprises an acceptor label, the donor label comprising a fluorescent molecule which is able to donate fluorescent energy to the acceptor label; and monitoring fluorescence of said sample. The method can be used to quantitate the amount of target nucleic acid in the sample as well as to determine sequence characteristics. Kits for effecting the method are also claimed.

17 Claims, 1 Drawing Sheet

Figure 1A:
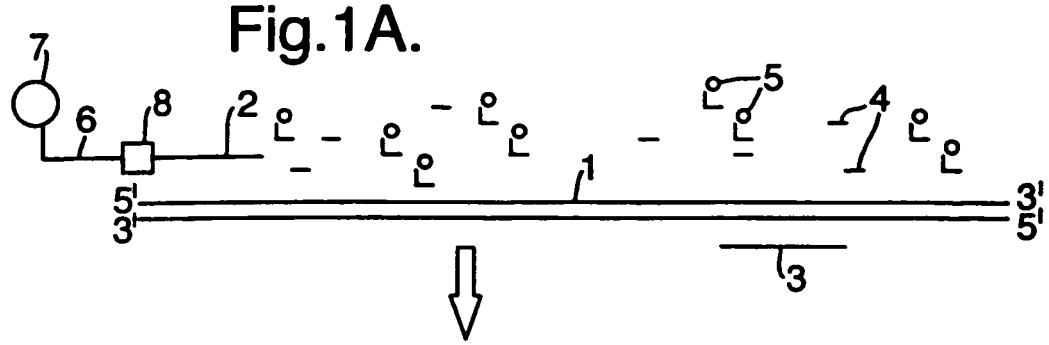
Figure 1B:
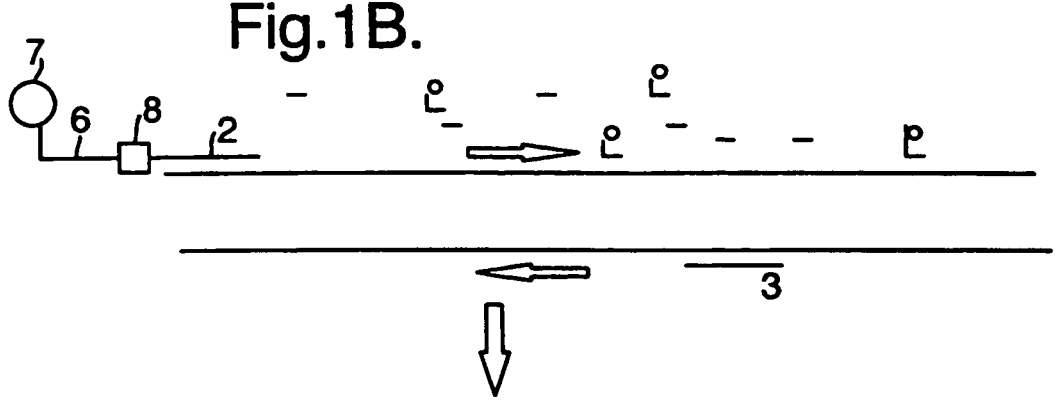

AMPLIFICATION METHOD FOR DETECTION OF TARGET NUCLEIC ACIDS INVOLVING-FLUORESCENCE ENERGY TRANSFER

This application claims priority to Great Britain Application No. 9918237.0 filed on Aug. 4, 1999 and International Application No. PCT/GB00/03016 filed on Aug. 3, 2000 and published in English as International Publication Number WO 01/11078 A1 on Feb. 15, 2001, the entire contents of each are hereby incorporated by reference.

The present invention provides a method for detecting a target polynucleotide in a sample, for example by monitoring an amplification reaction, preferably in a quantitative manner, as well as to probes and kits for use in these methods. The method is also suitable for the detection of sequence characteristics such as polymorphisms or allelic variation and so may be used in diagnostic methods.

Known fluorescence polymerase chain reaction (PCR) monitoring techniques include both strand specific and generic DNA intercalator techniques that can be used on a few second-generation PCR thermal cycling devices.

Generic fluorescence PCR methods utilise DNA intercalating dyes that exhibit increased fluorescence when bound to double stranded DNA species. Fluorescence increase due to a rise in the bulk concentration of DNA during amplifications can be used to measure reaction progress and to determine the initial target molecule copy number. Furthermore, by monitoring fluorescence with a controlled change of temperature, DNA melting curves can be generated, for example, at the end of PCR thermal cycling.

These generic fluorescence PCR methods monitor the rise in bulk concentration of nucleic acids without any time penalty. A single fluorescent reading can be taken at the same point in every reaction. End point melting curve analysis can be used to discriminate artefacts from amplicon, and to discriminate amplicons. Peaks of products can be seen at concentrations that cannot be visualised by agarose gel electrophoresis.

In order to obtain high resolution melting data, the melt experiment must be performed slowly on existing hardware taking up to five minutes. However, by continually monitoring fluorescence amplification, a 3D image of the hysteresis of melting and hybridisation can be produced. This 3D image is amplicon dependent and may provide enough information for product discrimination.

It has been found that DNA melting curve analysis in general is a powerful tool in optimising PCR thermal cycling. By determining the melting temperatures of the amplicons, it is possible to lower the denaturing temperatures in later PCR cycles to this temperature. Optimisation for amplification from first generation reaction products rather than the genomic DNA, reduces artefact formation occurring in later cycles. Melting temperatures of primer oligonucleotides and their complements can be used to determine their annealing temperatures, reducing the need for empirical optimisation.

The generic intercalator methods however are only quasi-strand-specific and are therefore not very useful where strand specific detection is required.

Fluorescence PCR strand specific methods utilise additional nucleic acid reaction components to monitor the progress of amplification reactions. These methods may use fluorescence energy transfer (FET) as the basis of detection. One or more nucleic acid probes are labelled with fluorescent molecules, one of which is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is excited at this emission wavelength such that it can accept the emission energy of the donor molecule by a variety of distance-dependent energy transfer mechanisms. A specific example of fluorescence energy transfer which can occur is Fluorescence Resonance Energy Transfer or "FRET". Generally the acceptor molecule accepts the emission energy of the donor molecule when they are in close proximity (e.g. on the same, or a neighbouring molecule). The basis of FET or FRET detection is to monitor the changes at donor emission wavelength. Where the acceptor is also a fluorescent molecule, the acceptor emission wavelengths may also be monitored.

There are two commonly used types of FET or FRET probes, those using hydrolysis of nucleic acid probes to separate donor from acceptor, and those using hybridisation to alter the spatial relationship of donor and acceptor molecules.

Hydrolysis probes are commercially available as TaqMan™ probes. These consist of DNA oligonucleotides which are labelled with donor and acceptor molecules. The probes are designed to bind to a specific region on one strand of a PCR product. Following annealing of the PCR primer to this strand, Taq enzyme extends the DNA with 5' to 3' polymerase activity. Taq enzyme also exhibits 5' to 3' exonuclease activity. TaqMan™ probes are protected at the 3' end by phosphorylation to prevent them from priming Taq extension. If the TaqMan™ probe is hybridised to the product strand than an extending Taq molecule may also hydrolyse the probe, liberating the donor from acceptor as the basis of detection. The signal in this instance is cumulative, the concentration of free donor and acceptor molecules increasing with each cycle of the amplification reaction.

The fact that signal generation is dependent upon the occurrence of probe hydrolysis reactions means that there is a time penalty associated with this method. Furthermore, the presence of the probe may interrupt the smooth operation of the PCR process.

In addition, it has been found that hydrolysis can become non-specific, particularly where large numbers of amplification cycles, for instance more than 50 cycles, are required. In these cases, non-specific hydrolysis of the probe will result in an unduly elevated signal.

This means that such techniques are not very compatible with rapid PCR methods which are becoming more prominent with the development of rapid hot air thermal cyclers such as the RapidCycler™ and LightCycler™ from Idaho Technologies Inc. Other rapid PCR devices are described for example in co-pending British Patent Application Nos. 9625442.0 and 9716052.7. The merits of rapid cycling over conventional thermal cycling have been reported elsewhere. Such techniques are particularly useful for example in detection systems for biological warfare where speed of result is important if loss of life or serious injury is to be avoided.

Furthermore, hydrolysis probes do not provide significant information with regard to hysteresis of melting since signal generation is, by and large, dependent upon hydrolysis of the probe rather than the melt temperature of the amplicon or probe.

Hybridisation probes are available in a number of guises. Molecular beacons are oligonucleotides that have complementary 5' and 3' sequences such that they form hairpin loops. Terminal fluorescent labels are in close proximity for FRET to occur when the hairpin structure is formed. Following hybridisation of molecular beacons to a complementary sequence the fluorescent labels are separated, so FRET does not occur, and this forms the basis of detection.

Pairs of labelled oligonucleotides may also be used. These hybridise in close proximity on a PCR product strand bringing donor and acceptor molecules together so that FRET can occur. Enhanced FRET is the basis of detection. Variants of this type include using a labelled amplification primer with a single adjacent probe.

The use of two probes, or a molecular beacon type of probe which includes two labelling molecules increases the cost involved in the process. In addition, this method requires the presence of a reasonably long known sequence so that two probes which are long enough to bind specifically in close proximity to each other are known. This can be a problem in some diagnostic applications, where the length of conserved sequences in an organism which can be used to design an effective probe, such as the HIV virus, may be relatively short.

Furthermore, the use of pairs of probes involves more complex experimental design. For example, a signal provided when by the melt of a probe is a function of the melting off of both probes. The study of small mismatches or where one of the probes is required to bind across a splice region (for example to detect RNA as compared to DNA in a sample where the sequence on either side of an intron can be utilised as the probe site) can yield incorrect results if the other probe melts first.

Copending International Patent application No. PCT/GB990504 describes assay for detecting the presence of particular nucleic acid sequences which may be adapted to quantify the amount of the target sequence in the sample. In this assay, an amplification reaction is effected using a set of nucleotides, at least one of which is fluorescently labelled. Thus the amplification product has fluorescent label incorporated in it. The reaction is effected in the presence of a probe which can hybridise to the amplification product and which includes a reactive molecule which is able to absorb fluorescence from or donate fluorescent energy to said fluorescent labelled nucleotide. The reaction can then be monitored by measuring the fluorescence of said sample as this will alter during the course of the reaction as more product is formed which hybridises to the probe and gives rise to a FET or FRET interaction between them.

The applicants have now found an improved way of effecting said assay.

The invention provides a method for detecting the presence of a target nucleic acid sequence in a sample, said method comprising subjecting said sample to an amplification reaction using a set of nucleotides, at least one of which is labelled with a first label, and a reagent comprising an amplification primer which can hybridise to said target sequence when in single stranded form and which is connected at its 5' end to a probe which carries a second label by way of a chemical linking group, said labelled probe being of a sequence which is similar to that of the said target sequence, such that it can hybridise to a complementary region in an amplification product, and wherein one of the first or the second label comprises a fluorescent molecule which is able to donate fluorescent energy to the other of said first or second label; and monitoring fluorescence of said sample.

In this assay, in a first stage, the target sequence is made single stranded so that the primer region of the reagent can hybridise to it. This can thus initiate extension of the strand to generate a complementary strand which will include labelled nucleotides and will also have a labelled probe region upstream of its 5' end which is complementary to a downstream region of the product.

Once the extension phase is complete, the product is separated from its template strand during a melt phase and so becomes single stranded. In this form, the labelled probe region is able to twist over and hybridise to the complementary region of the product strand whereupon the label which is able to donate fluorescent energy (donor) to the other label by means of FET or FRET does so, thus changing the fluorescent signal from the sample. This change in signal can be monitored throughout the reaction in order to monitor the progress of the amplification reaction.

In the second and subsequent stages of the amplification, the product strand may itself act as a template strand for extension. However, the chemical link will halt the extension reaction before a sequence complementary to said probe is produced. Thus the probe region remains single stranded.

If required, a corresponding amplification primer which is not attached to a labelled probe region may also be present during the amplification reaction. This primer would result in the production of a conventional unlabelled amplification product which may serve to mediate the signal into the dynamic range of the detector device being used. It may also improve reaction efficiency which may be adversely affected by the presence of a complex probe/primer structure.

When the label which is able to absorb fluorescence from the donor label (acceptor) performs this function, fluorescence from the donor is reduced. This reduction may be detected and this indicates binding of the probe region.

Most preferably, the label which is able to absorb fluorescence (acceptor) is itself a fluorescent molecule which emits fluorescence at a characteristic wavelength. In this case, increase in fluorescence from the acceptor molecule, which is of a different wavelength to that of the donor label, will also indicate binding of the probe.

Suitably, the donor label is provided on the nucleotides and the acceptor label is provided on the probe. In this case, the presence of the thus labelled amplification product can be detected by monitoring fluorescence from the acceptor molecule on the probe, which predominantly binds to a downstream region of the same product strand. In this case, signal from the amplification product can be distinguished from background signal of the fluorescent label and also from any non-specific amplification product.

The fact that the signal is produced only by labelled amplification product means that the system is highly specific in terms of detecting specific target sequences in reaction mixtures that contain large amounts of background DNA. This is because non-specific amplification product will not hybridise to the probe region and so does not contribute to the measured signal.

An assay of this nature can be carried out using inexpensive reagents. Single labelled probes are more economical than those which include both acceptor and donor molecules.

The labelled probe within the reagent may be single stranded or it may include a complementary 5' and 3' sequences such that it takes the form of a molecular beacon as described above. In this case, however, the probe requires only one label molecule as the FET or FRET signal forming the basis of the detection arises as a result of the interaction between the label on the probe and the labelled nucleotides within the amplicon strand.

As used herein, the expression "set of nucleotides" refers to a group of nucleotides which are sufficient to form nucleic acids such as DNA and RNA and other analogues. Thus these comprise adenosine, cytosine, guanine and thymine or uracil-containing nucleotides. One or more of these is fluorescently labelled. Labelled uracil is available from Boehringer Mannheim. Suitable fluorescent labels include fluorescein.

The use of labelled uracil may be particularly preferred in that its use may be built into the a strategy for preventing contamination or carry-over from one amplification reaction to subsequent ones carried out in the reaction vessels. Enzymes which digest uracil containing nucleic acids, such as uracil-N-glycosylase, can be used in a pre-cycling incubation step, to ensure that any residual amplicons are digested before thermal cycling in the subsequent application begins.

Suitably more than one nucleotide, and possibly all the nucleotides are labelled as this will moderate the level of signal from the amplification product and thus the FET or FRET signal.

Amplification is suitably effected using known amplification reactions such as the polymerase chain reaction (PCR) or the ligase chain reaction (LCR), strand displacement assay (SDA) or NASBA, but preferably PCR.

Preferably, the fluorescence of both the first and second labels (i.e. both the donor and the acceptor labels) are monitored and the relationship between the emissions calculated.

Suitable acceptor labels are fluorescent dyes such as rhodamine dyes or other dyes such as Cy5. Alternatively, the acceptor label may comprise a non-fluorescent acceptor molecule, sometimes known as a "dark acceptor" such as DABCYL or Methyl Red. These may be attached to the probe in a conventional manner. The position of the acceptor label along the probe is immaterial although it general, they will be positioned at an end region of the probe.

In order for FET, such as FRET, to occur between the first and second labels, the fluorescent emission of the donor label must be of a shorter wavelength than the acceptor label.

Suitable combinations are therefore set out in the following Table:

| Donor | Acceptor |
| --- | --- |
| SYBRGold | rhodamine |
| SYBRGreen I | rhodamine |
| Fluorescein | rhodamine |
| SYBRGold | Cy5 |
| SYBRGreen I | Cy5 |
| Fluorescein | Cy5 |
| Fluorescein | Ethidium bromide |
| Fluorescein | Dabcyl |
| Fluorescein | Methyl Red |
| Fluroescein | QSY-7 diaryl rhodamine dyes* |

*Available from Molecular Probes, UK.

Preferably, the molecules used as donor and/or acceptor produce sharp emission peaks, and there is little or no overlap in the wavelengths of the emission. Under these circumstances, it may not be necessary to resolve the "strand specific peak" from the signal produced by amplification product. A simple measurement of the strand specific signal alone (i.e. that provided by the acceptor label) will provide information regarding the extent of the FET or FRET caused by the target reaction.

However, where there is a spectral overlap in the fluorescent signals from the donor and acceptor labels, this can be accounted for in the results, for example by determining empirically the relationship between the spectra and using this relationship to normalise the signals from the two signals.

The chemical link separating the labelled probe from the primer is suitably any molecule that can link nucleotide sequences but which is not recognised by a DNA polymerase. A wide range of chemical linkers which would fulfil this requirement are available.

Examples of the types of chemical and reactions which may be used in the formation of linkers are described for example in WO 95/08642. In particular, the chemical linker comprises a group of atoms joining the two polynucleotide sequences, (primer and probe) together. The linker can be joined to the respective polynucleotide sequences by any of the conventional methods.

Generally speaking, the linker will be derived from an organic chemical having a first and a second functional group by means of which it can be attached to the probe and the primer sequences respectively or to individual nucleotides from which the probe or primer sequence is then generated subsequently.

Attachment of the linker can be for example by means of a carbon—carbon single bond, carbon—carbon double bond, carbon—carbon triple bond, carbon-nitrogen single bond, carbon-nitrogen double bond, carbon-oxygen single bond, carbon-sulphur single bond, carbon-silicon single bond, sulphur-nitrogen bond, sulphur-oxygen bond, phosphorous-oxygen bond, or phosphorous-nitrogen bond, depending upon the nature of the organic chemical and the reaction used in forming the linker.

Suitable functional groups include but are not limited to, hydroxyl groups, amino groups, thio groups, alkyl sulphates, and halides.

Suitably, the linker may be introduced in stages.

For example, the organic chemical having a first functional group but with a second functional group blocked, (for example as alcohol, ester, thioalkyl etc. groups) can be reacted with either the probe or the primer sequences in order to attach it to an end thereof. Following removal of the blocking group using conventional methods, the second functional group may be reacted with the other of the probe or the primer to form a chemical linker therebetween.

Alternatively, the chemical linker may be generated in situ from two parts, for example using the following reaction scheme:

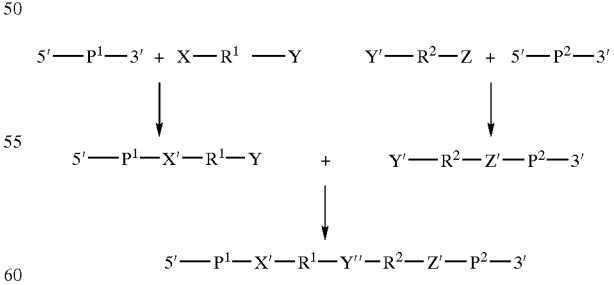

where $p^1$ and $p^2$ represent primer and probe polynucleotide sequences; X is a functional group which reacts with a 3' end of a polynucleotide sequence to form a moiety —X'—, Z is a functional group which reacts with a 5' end of a polynucleotide sequence to form a moiety —Z'—, Y and Y' are functional groups which do not react with polynucleotides but react with each other to form a group Y", and R¹ and R² are parts of the linker.

Depending upon the nature of the reaction taking place, X', Y" or Z' may be direct bonds. Examples of suitable groups R¹ and/or R² include:

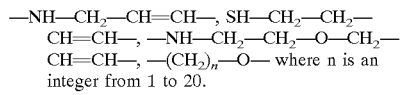
—NH—CH₂—CH=CH—, SH—CH₂—CH₂—
CH=CH—, —NH—CH₂—CH₂—O—CH₂—
CH=CH—, —(CH₂)ₙ—O— where n is an integer from 1 to 20.

Where the linker is attached to the 5' or 3' terminus of the polynucleotide, convenient linkages include phosphate, carboxy or ether linkages, particularly phosphate linkages. Suitable phosphate linkers include aminoalkylphosphoryl groups, especially those comprising a $C_{1-12}$ alkyl chain, especially a $C_6$ alkyl chain. These linkers may be readily attached to synthetic oligonucleotides during solid-phase synthesis, see for example S. Agrawal et al, Nucleic Acids Research, 1986, 14, 6227 and WO-88/02004 (Applied Biosystems).

Other general methods for attaching a linker onto a polynucleotide base are discussed in J. L. Ruth and D. E. Bergstrom, J. Org. Chem., 1978, 43, 2870; D. E. Bergstrom and M. K. Ogawa, J. Amer. Chem. Soc., 1978, 10, 8106; and C. F. Bigge, P. Kalaritis, J. R. Deck and M. P. Mertes, J. Amer. Chem. Soc., 1980, 102, 2033. One preferred method is the one disclosed in detail in European Patent Application No. 063,879. The method involves reacting a linker or a linker fragment containing an alpha-vinyl groups with a mercurated base in the presence of $K_2PdCl_4$, wherein the mercury is bound as Hg+ to the position of the base which is to react with the linker.

The size or content of the linker can be varied considerably provided that it can act as a block to extension whilst allowing hybridisation between the probe region and the target sequence. The linker can contain from about two carbons to any number of carbons, for example up to 20 atoms. The linker can contain heteroatoms and unsaturations. Aliphatic, alicyclic, aromatic or heterocyclic groups may be present in the chemical linker. It conveniently comprises —(CH₂)ₙ—. It may however include other groups such as —O—, —CHOH—, —COO—, and —CH₂CH₂—O— which help maintain water solubility.

Attachment of the linker to the sugar group of a polynucleotide can be by means of a Schiff base to the 1'-aldehyde following depurination or depyrimidation of preselected bases or it can be to the 2'-hydroxy in the case when the sugar is ribose. Attachment of a linker arm to the phosphate moiety can be by alkylation of the phosphate groups, for example as described in U.S. Pat. No. 4,469,863.

In order to attach a chemical linker to the base group of a polynucleotide, it may be preferable to attach it to the base before formation of the polynucleotide. This is because the reaction conditions that may be required to attach the linker to the base may cause undesirable side reactions in a polynucleotide. Furthermore, attachment at the polynucleotide level may give inconsistent and irreproducible yields. Attachment at the nucleotide or nucleotide level permits the modified nucleoside or nucleotide to first be purified and then to be incorporated into a polynucleotide. The incorporation can either be by cloning, for example, in a M13 vector, or by synthesis in a polynucleotide synthesiser instrument in a conventional manner.

When the linker is attached to the 1'-aldehyde of a sugar, the linker is suitably attached following the formation of the polynucleotide portion of the polynucleotide probe. This is because attachment of the sugar requires a free aldehye at the 1'-position of the sugar. The free aldehyde is formed by depurination or depyrimidation. A group comprising a sugar and a phosphate without a base is not a substrate for the polymerase enzymes. Thus the linker must be attached by first selectively depurinating or depyrimidinating the desired polynucleotide sequence and then attaching the linker to the sugar by means of the aldehyde. When the linker is attached to the 2'-hydroxy group of a ribose sugar, the linker can be attached at the nucleoside, nucleotide or polynucleotide level.

This is because nucleotides modified by a linker can be incorporated into a polynucleotide by means of a polynucleotide synthesiser instrument. When the linker arm is attached to the phosphate, the linker arm is preferably attached at the nucleoside or nucleotide level so that the attachment is not at positions other than at a phosphate. Phosphoramidite technology may be used in a nucleic acid synthesiser to incorporate the linker to the 5' or 3' end of a polynucleotide.

In particular, the linkers will comprises a multiple form of ethylene glycol, for example Hex ethylene glycol. Such linkers may be of structure —(CHOH—CHOH)ₙ— where n is an integer in excess of 1, for example from 1–10 and suitably 6.

Probes comprising linker groups can be obtained from Oswell Ltd, UK.

The method of the invention is extremely versatile in its applications. The method can be used to generate both quantitative and qualitative data regarding the target nucleic acid sequence in the sample, as discussed in more detail hereinafter. In particular, not only does the invention provide for quantitative amplification, but also it can be used, additionally or alternatively, to obtain characterising data such as duplex destabilisation temperatures or melting points.

In the method of the invention, the labelled probe is integral with an amplification primer and so is present throughout the course of the amplification reaction. The process allows the detection to be effected in a homogenous manner, in that the amplification and monitoring can be carried out in a single container with all reagents added initially. No subsequent reagent addition steps are required. Neither is there any need to effect the method in the presence of solid supports (although this is an option as discussed further hereinafter).

Since the probe is present throughout the amplification reaction, the fluorescent signal may allow the progress of the amplification reaction to be monitored. This may provide a means for quantitating the amount of target sequence present in the sample.

During each cycle of the amplification reaction, amplicon strands containing the target sequence and a probe region generate an acceptor signal. As the amount of such amplicons in the sample increases, so the acceptor signal will increase. By plotting the rate of increase over cycles, the start point of the increase can be determined.

The labelled probe may comprise a nucleic acid molecule such as DNA or RNA, which will hybridise to the target nucleic acid sequence when the latter is in single stranded form. In this instance, step (b) will involve the use of conditions which render the target nucleic acid single stranded. Alternatively, the probe may comprise a molecule such as a peptide nucleic acid or another nucleic acid analogue which also binds the target sequence in double stranded form.

In particular, the amplification reaction used will involve a step of subjecting the sample to conditions under which any of the target nucleic acid sequence present in the sample becomes single stranded, such as PCR or LCR. It is possible then for the probe region to hybridise to the downstream region of the amplicon strand containing it during the course of the amplification reaction provided appropriate hybridisation conditions are encountered.

In a preferred embodiment, the probe may be designed such that these conditions are met during each cycle of the amplification reaction. Thus at some point during each cycle of the amplification reaction, the probe will hybridise to the target sequence, and generate a signal as a result of the FET or FRET. As the amplification proceeds, the probe region will be separated or melted from the downstream sequence and so the signal generated by the acceptor label will either reduce or increase depending upon whether it comprises the donor or acceptor molecule. For instance, where it is an acceptor, in each cycle of the amplification, a fluorescence peak from the acceptor label is generated. The intensity of the peak will increase as the amplification proceeds because more amplicon strands including probes becomes available.

By monitoring the fluorescence of the acceptor label from the sample during each cycle, the progress of the amplification reaction can be monitored in various ways. For example, the data provided by melting peaks can be analysed, for example by calculating the area under the melting peaks and this data plotted against the number of cycles.

Fluorescence is suitably monitored using a known fluorimeter. The signals from these, for instance in the form of photo-multiplier voltages, are sent to a data processor board and converted into a spectrum associated with each sample tube. Multiple tubes, for example 96 tubes, can be assessed at the same time. Data may be collected in this way at frequent intervals, for example once every 10 ms, throughout the reaction.

The spectra generated in this way can be resolved, for example, using "fits" of pre-selected fluorescent moieties such as dyes, to form peaks representative of each signalling moiety (i.e. nucleotide label and/or probe label). The areas under the peaks can be determined which represents the intensity value for each signal, and if required, expressed as quotients of each other. The differential of signal intensities and/or ratios will allow changes in FET or FRET to be recorded through the reaction or at different reaction conditions, such as temperatures. The changes, as outlined above, are related to the binding phenomenon between the probe and the target sequence. The integral of the area under the differential peaks will allow intensity values for the FET or FRET effects to be calculated.

This data provides one means to quantitate the amount of target nucleic acid present in the sample.

The primer/labelled probe reagent may either be free in solution or immobilised on a solid support, for example on the surface of a bead such as a magnetic bead, useful in separating products, or the surface of a detector device, such as the waveguide of a surface plasmon resonance detector. The selection will depend upon the nature of the particular assay being looked at and the particular detection means being employed.

The probe may be designed such that it is hydrolysed by the DNA polymerase used in the amplification reaction thereby releasing the acceptor molecule. This provides a cumulative signal, with the amount of free probe label present in the system increasing with each cycle. However, it is not necessary in this assay for the probe to be consumed in this way as the signal does not depend upon the hydrolysis of the probe.

Suitably, the probe is designed such that it is released intact from the target sequence and so is able to bind again when suitable hybridisation conditions are met during the amplification reaction. This may be, for example, during the extension phase of the amplification reaction. However, since the signal is not dependent upon probe hydrolysis, the probe may be designed to hybridise and melt from the target sequence at any stage during the amplification cycle. In particular, the probe will be designed to hybridise at temperatures above the extension temperature of the reaction as this will ensure that interference with the amplification reaction is minimised.

This provides a fully reversible signal which is directly related to the amount of amplification product present at each stage of the reaction. Furthermore, it is advantageous where speed of reaction is of the greatest importance, for example in rapid PCR, since a probe which is integral with the amplicon strand being detected will be able to hybridise rapidly to it.

The data generated in this way can be interpreted in various ways. In its simplest form, an increase in fluorescence of the acceptor molecule in the course of or at the end of the amplification reaction is indicative of an increase in the amount of the target sequence present, suggestive of the fact that the amplification reaction has proceeded and therefore the target sequence was in fact present in the sample. However, as outlined above, quantitation is also possible by monitoring the amplification reaction throughout. Finally, it is possible to obtain characterisation data and in particular melting point analysis, either as an end point measure or throughout, in order to obtain information about the sequence as will be discussed further below.

Thus, a preferred embodiment of the invention comprises a method for detecting nucleic acid amplification comprising: performing nucleic acid amplification on a target polynucleotide in the presence of (a) a nucleic acid polymerase, (b) a set of nucleotides, at least one of which is labelled with a first label and (c) a reagent comprising an amplification primer which can hybridise to said target sequence when in single stranded form and which is connected at its 5' end to a probe which carries a second label, by way of a chemical linking group, said labelled probe being of a sequence which is similar to that of the said target sequence, such that it can hybridise to a complementary region in an amplification product, and wherein one of the first or second labels comprises a donor label which is able to donate fluorescent energy to the other of the first or second labels which comprises an acceptor label able to absorb fluorescent energy from said donor molecule, said primer being capable of hybridising to said target polynucleotide; and monitoring changes in fluorescence during the amplification reaction. Suitably, the acceptor label is itself fluorescent and emits fluorescent energy at a characteristic wavelength.

The amplification is suitably carried out using a pair of primers which are designed such that only the target nucleotide sequence within a DNA strand is amplified as is well understood in the art. The nucleic acid polymerase is suitably a thermostable polymerase such as Taq polymerase.

Suitable conditions under which the amplification reaction can be carried out are well known in the art. The optimum conditions may be variable in each case depending upon the particular amplicon involved, the nature of the primers used and the enzymes employed. The optimum conditions may be determined in each case by the skilled person. Typical denaturation temperatures are of the order of 95° C., typical annealing temperatures are of the order of 55° C. and extension temperatures are of the order of 72° C.

In a particular embodiment of the invention the labelled probe may be used to quantitate RNA transcripts, for example in expression experiments, that maybe used in drug discovery. In particular this embodiment is suitable for expression studies in tissues from eukaryotic organisms. DNA encoding proteins in eukaryotic cells may contain introns, non-coding regions of DNA sequence, and exons that encode for protein sequence. Noncoding intron sequences are removed from RNA sequences that are derived from the DNA sequences during cellular "splicing" processes. PCR primers are normally targeted at coding regions and when reverse transcriptase PCR is used on total nucleic acid extracts, products will result from both DNA dependent amplification and RNA dependent amplification. Thus PCR alone, when used for expression studies, will contain amplification resulting from genomic DNA and expressed RNA.

A labelled probe that is designed to bind across introns, on adjacent terminal regions of coding exons, will have limited interaction because of the intron region. Spliced RNA has these regions removed and therefore the adjacent terminal regions of coding exons form one continuous sequence allowing efficient binding of the probe region.

Conversely, the probe region may detect only an amplification product of genomic DNA if it is designed such that it binds an intron region. Signal generated from such a probe would relate only to the DNA concentration and not the RNA concentration of the sample.

Thus in a further embodiment, the probe region is specific either for a splice region of RNA or an intron in DNA, so that only one of amplified RNA or amplified DNA is detected and/or quantitated.

Alternatively or additionally, the method of the invention can be used in hybridisation assays for determining characteristics of a sequence. Thus in a further aspect, the invention provides a method for determining a characteristic of a sequence, said method comprising (a) amplifying said sequence using a set of nucleotides, at least one of which is labelled with a first label, and a reagent comprising an amplification primer linked by way of a chemical link at its 5' end to a probe which comprises a sequence which is similar to that of a region of the target sequence and which further comprises a second label, where one of said first or second labels is a donor label and the other is an acceptor label, the donor label being able to donate fluorescent energy to the acceptor label; so as to form an amplification product incorporating a probe region, (b) subjecting amplification product to conditions under which the probe region thereof will hybridise to the complementary region of the amplification product, and (c)monitoring fluorescence of said sample and determining a particular reaction condition, characteristic of said sequence, at which fluorescence changes as a result of the hybridisation of the probe region to the sample or destabilisation of the duplex formed between the probe region and the target nucleic acid sequence.

Suitable reaction conditions include temperature, electrochemical, or the response to the presence of particular enzymes or chemicals. By monitoring changes in fluorescence as these properties are varied, information characteristic of the precise nature of the sequence can be achieved. For example, in the case of temperature, the temperature at which the probe separates from the sequences in the sample as a result of heating can be determined. This can be extremely useful in for example, to detect and if desired also to quantitate, polymorphisms and/or allelic variation in genetic diagnosis. By "polymorphism" is included transitions, transversions, insertions, deletions of inversions which may occur in sequences, particularly in nature.

The hysteresis of melting will be different if the target sequence varies by only one base pair. Thus for example, where a sample contains only a single allelic variant, the temperature of melting of the probe region will be a particular value which will be different from that found in a sample which contains only another allelic variant. A sample containing both allelic variants which show two melting points corresponding to each of the allelic variants. Similar considerations apply with respect to electrochemical properties, or in the presence of certain enzymes or chemicals. The labelled probe may be immobilised on a solid surface across which an electrochemical potential may be applied. Downstream target sequence will bind to or be repulsed from the probe at particular electrochemical values depending upon the precise nature of the sequence.

In addition, the kinetics of probe hybridisation will allow the determination, in absolute terms, of the target sequence concentration. Changes in fluorescence from the sample can allow the rate of hybridisation of the probe region to the sample to be calculated. An increase in the rate of hybridisation will relate to the amount of target sequence present in the sample. As the concentration of the target sequence increases as the amplification reaction proceeds, hybridisation of the probe region will occur more rapidly. Thus this parameter may also be used as a basis for quantification. This mode of data processing useful in that it is not reliant directly on signal intensity to provide the information.

Further aspects of the invention include kits for use in the method of the invention. These kits will contain a probe specific for a target nucleotide sequence which contains a label, in particular an acceptor label, linked to the 5' end of an amplification primer. If desired, the probe can be immobilised on a support such as a bead, for example a magnetic bead, or a support used in a detector, such as the waveguide of an evanescent wave detector device.

Additionally, kits may contain one or more labelled nucleotides, in particular fluorescently labelled nucleotides which is/are compatible with said acceptor labels. Other potential components of the kit include reagents used in amplification reactions such as a DNA polymerase.

The use of a non-fluorescent acceptor molecule may also be used in the assay described in copending International Patent Application No PCT/GB990504.

Thus in a further aspect, the invention provides a method for detecting the presence of a target nucleic acid sequence in a sample, said method comprising (a) subjecting said sample to an amplification reaction using a set of nucleotides, at least one of which is labelled with a first label, (b) contacting amplification product with a probe under conditions in which the probe will hybridise to said target sequence, said probe comprising a second label molecule, one or said first or second label being fluorescent and the other being a non-fluorescent molecule which is able to accept fluorescent energy therefrom and (c)monitoring fluorescence of said sample.

Suitably, the non fluorescent label is DABCYL, Maruric (Methyl) red or a QSY-7 diarylrhodamine dye. The non-fluorescent label is preferably the second label and is provided on the probe.

The invention will now be particularly described by way of example with reference to the accompanying diagrammatic drawings in which:

FIG. 1 shows diagrammatically the interactions which take place in the method of the invention.

In the illustrated amplification reaction, a DNA molecule (1) prepared for amplification by contacting it with pair of amplification primers (2), (3) and a set of nucleotides (4) some of which are labelled with a fluorescent label (5). One of the primers (2) is linked to a probe (6) which includes a acceptor label (7) by way of a chemical link (8).

The DNA molecule (1) is rendered single stranded (FIG. 1B) whereupon the primers (2, 3) bind as forward and reverse primers in an amplification reaction as is well known.

Figure 1C:
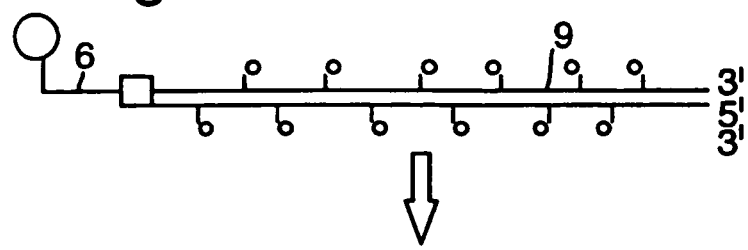

During the course of the subsequent amplification reaction, an amplicon product (9) is built up (FIG. 1C). Nucleotides both labelled and unlabelled are incorporated into the product as it is formed. A significant proportion of the amplicon strands will include a labelled probe region (6, 7).

Figure 1D:
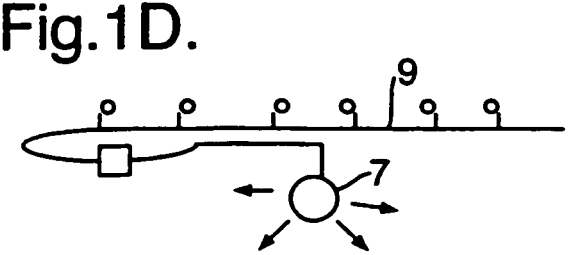

When this product is melted during the subsequent phase of the amplification, the probe region (6) comprising an acceptor molecule (7) binds the target sequence within the amplicon strand (FIG. 1D). The FRET interaction between the fluorescent nucleotides and the acceptor molecule (7) generates a signal at the wavelength characteristic of the acceptor.

The signal from the acceptor molecule (7) can then be monitored using conventional fluorescence detection devices.

The invention claimed is:

1. A method for detecting the presence of a target nucleic acid sequence in a sample, said method comprising subjecting said sample to an amplification reaction using a set of nucleotides, at least one of which is labelled with a first label, and a reagent comprising an amplification primer which can hybridise to said target sequence when in single stranded form and which is connected at its 5' end to a probe which carries a second label by way of a chemical linking group, said labelled probe being of a sequence which is similar to that of the said target sequence, such that it can hybridise to a complementary region in an amplification product, and wherein one of the first or the second label comprises a donor label and the other comprises an acceptor label, the donor label comprising a fluorescent molecule which is able to donate fluorescent energy to the acceptor label; and monitoring fluorescence of said sample.

2. A method according to claim 1 wherein the said first label comprises a donor label and said second label comprises the acceptor label.

3. A method according to claim 1 wherein the acceptor label is a fluorescent molecule which emits energy at a characteristic wavelength.

4. A method according to claim 3 wherein the acceptor label is a rhodamine dye or other dyes such as Cy5.

5. A method according to claim 1 wherein the acceptor label is a dark acceptor such as DABCYL, Methyl Red or a QSY-7 diarylrhodamine dye.

6. A method according to claim 1 wherein the labelled nucleotide is labelled uracil-containing nucleotide.

7. A method according to claim 1 wherein all nucleotides used in the amplification reaction are labelled.

8. A method according to claim 1 wherein the amplification reaction comprises the polymerase chain reaction (PCR).

9. A method according to claim 1 wherein the acceptor molecule is a fluorescent molecule and wherein fluorescence of both the donor and the acceptor molecules are monitored and the relationship between the emissions calculated.

10. A method according to claim 1 wherein the fluorescent signal from the sample is monitored throughout the amplification reaction and the results used to quantitate the amount of target sequence present in the sample.

11. A method for detecting nucleic acid amplification comprising: performing nucleic acid amplification on a target polynucleotide in the presence of (a) a nucleic acid polymerase, (b) a set of nucleotides, at least one of which is labelled with a first label and (c)a reagent comprising an amplification primer which can hybridise to said target sequence when in single stranded form and which is connected at its 5' end to a probe which carries a second label, by way of a chemical linking group, said labelled probe being of a sequence which is similar to that of the said target sequence, such that it can hybridise to a complementary region in an amplification product, and wherein one of the first or second labels comprises a donor label which is able to donate fluorescent energy to the other of the first or second labels which comprises an acceptor label able to absorb fluorescent energy from said donor molecule, said primer being capable of hybridising to said target polynucleotide; and monitoring changes in fluorescence during the amplification reaction.

12. A method according to claim 11 wherein the amplification is carried out using a pair of primers which are designed such that only the target nucleotide sequence within a DNA strand is amplified.

13. A method according to claim 1 wherein the probe is specific either for a splice region of RNA or an intron in DNA, so that only one of amplified RNA or amplified DNA is detected and/or quantitated.

14. A method for determining a characteristic of a sequence, said method comprising (a) amplifying said sequence using a set of nucleotides, at least one of which is labelled with a first label, and a reagent comprising an amplification primer linked by way of a chemical link at its 5' end to a probe which comprises a sequence which is similar to that of a region of the target sequence and which further comprises a second label, where one of said first or second labels is a donor label and the other is an acceptor label, the donor label being able to donate fluorescent energy to the acceptor label; so as to form an amplification product incorporating a probe region, (b) subjecting amplification product to conditions under which the probe region thereof will hybridise to the complementary region of the amplification product, and (c)monitoring fluorescence of said sample and determining a particular reaction condition, characteristic of said sequence, at which fluorescence changes as a result of the hybridisation of the probe region to the sample or destabilisation of the duplex formed between the probe region and the target nucleic acid sequence.

15. A method for detecting a polymorphism and/or allelic variation, said method comprising amplifying a sequence suspected of containing said polymorphism or variation using a method as defined in claim 1, measuring the temperature at which the probe region melts from its complementary sequence within the amplification product using the fluorescent signal generated, and relating this to the presence of a polymorphism or allelic variation.

16. A method according to claim 2 wherein the acceptor label is a fluorescent molecule which emits energy at a characteristic wavelength.

17. A method according to claim 2 wherein the acceptor label is a dark acceptor such as DABCYL, Methyl Red or a QSY-7 diarylrhodamine dye.

* * * * *